US009510590B2

(12) United States Patent
Storm et al.

(10) Patent No.: US 9,510,590 B2
(45) Date of Patent: Dec. 6, 2016

(54) DELIVERY OF COMPOSITIONS TO ARTHROPODS

(75) Inventors: Clare Gillian Storm, Winchester (GB); Nicola Jane Huggett, Winchester (GB)

(73) Assignee: Exosect Limited, Winchester (GB)

( * ) Notice: Subject to any disclaimer, the term of this patent is extended or adjusted under 35 U.S.C. 154(b) by 558 days.

(21) Appl. No.: 13/817,747

(22) PCT Filed: Aug. 11, 2011

(86) PCT No.: PCT/GB2011/001209
§ 371 (c)(1), (2), (4) Date: May 8, 2013

(87) PCT Pub. No.: WO2012/022931
PCT Pub. Date: Feb. 23, 2012

(65) Prior Publication Data

US 2013/0224275 A1 Aug. 29, 2013

(30) Foreign Application Priority Data

Aug. 19, 2010 (GB) .................................. 1013880.8

(51) Int. Cl.
*A01N 25/12* (2006.01)
*A01N 25/08* (2006.01)

(52) U.S. Cl.
CPC ............... *A01N 25/12* (2013.01); *A01N 25/08* (2013.01)

(58) Field of Classification Search
CPC .............................. A01N 25/08; A01N 25/12
See application file for complete search history.

(56) References Cited

U.S. PATENT DOCUMENTS

| | | | | |
|---|---|---|---|---|
| 2008/0213329 | A1* | 9/2008 | Hamilton Baxter | 424/418 |
| 2009/0060880 | A1 | 3/2009 | Meikle et al. | |
| 2010/0062944 | A1* | 3/2010 | Webster | 504/358 |

FOREIGN PATENT DOCUMENTS

| | | | |
|---|---|---|---|
| GB | 2 268 676 | A | 1/1994 |
| GB | 2 425 954 | A | 11/2006 |
| GB | 2 436 288 | A | 9/2007 |
| JP | 09-040512 | A | 7/1995 |
| JP | 07-242502 | A | 9/1995 |
| JP | 2001-114614 | A | 4/2001 |
| WO | 97/33472 | A1 | 9/1997 |
| WO | 03/055315 | A1 | 7/2003 |
| WO | 2008/062221 | A2 | 5/2008 |
| WO | 2011/128639 | A2 | 10/2011 |
| WO | 2011/157983 | A1 | 12/2011 |

OTHER PUBLICATIONS

William G Meikle et al: "Impact of two treatments of a formulation of Beauveria bassiana (Deuteromycota: Hyphomycetes) conidia on Varroa mites (Acari: Varroidae) and on honeybee (Hymenoptera: Apidae) colony health", Experimental and Applied Acarology, pp. 105-117, May 28, 2008, vol. 46, No. 1-4.

* cited by examiner

*Primary Examiner* — Michael B Pallay
(74) *Attorney, Agent, or Firm* — Sughrue Mion, PLLC

(57) ABSTRACT

A method of delivering a biologically active chemical agent to an arthropod pest of a bee, comprising exposing a surface of the said bee to carnauba wax particles having a volume mean diameter of at least 10 μm comprising at least one biologically active chemical agent, wherein the bee delivers the biologically active chemical agent to the arthropod pest, characterized in that the carnauba wax particles consist essentially of 89.5-99.4% by weight of carnauba wax; ≤10% by weight of biologically active chemical agent; and 0.5% by weight of flow agent.

18 Claims, 2 Drawing Sheets

DELIVERY OF COMPOSITIONS TO ARTHROPODS

CROSS REFERENCE TO RELATED APPLICATIONS

Figure 1:
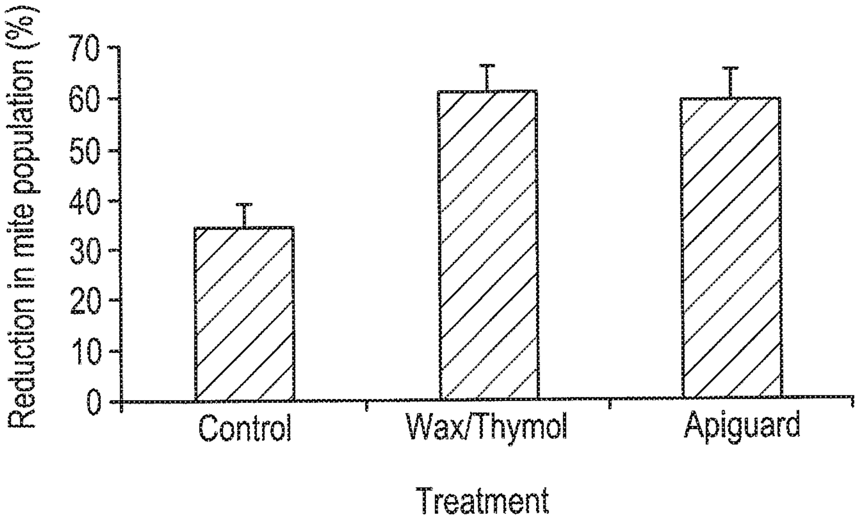

This application is a National Stage of International Application No. PCT/GB2011/001209 filed Aug. 11, 2011, claiming priority based on British Patent Application No. 10 13 880.8 filed Aug. 19, 2010, the contents of all of which are incorporated herein by reference in their entirety.

The present invention relates to a method of delivering a biologically active chemical agent in close association with a particle to an arthropod through the use of a bee as the particle carrying vector. In particular, the invention relates to the use of carnauba wax as a carrier particle for a biologically active chemical agent wherein the level or concentration of the biologically active chemical agent is such that honey flow is substantially uninterrupted and the health of the bees in the hive is not substantially compromised.

'Honey flow' is a term of art and is used to indicate that one or more major nectar sources are in bloom and the weather is favourable for bees to fly and collect the nectar. While the nectar sources are in bloom and the weather is suitable for bee flight, each bee will make several trips per day to the nectar source. As each bee collects pollen and nectar from the nectar source, it may acquire undesirable passenger arthropods, such as mites, which are then transported back to the hive where they may breed, infesting other bees and bee larvae in the brood chambers. When a bee hive is infested with undesirable arthropods such as *varroa* mites, bee health and honey yield can be severely compromised and often can result in the death of the entire hive.

There are a number of known methods for controlling arthropod pests of honey bees, but such methods do not appear to be sensitive to the need to maintain honey flow. Furthermore, such methods do not appear to address the need of ensuring that the level of deliberately introduced arthropod-controlling compounds required to maintain or improve the health of the hive is present at a zero level or a low level in the honey that is produced. Honey is analysed by regulatory bodies for contaminants such as biologically active chemical agents used against arthropod pests of the bee and the level of such chemical agents needs to be low to pass tests that are employed by the regulatory bodies. As a consequence there is a trade off between bee health on the one hand and honey quality on the other: it is therefore of interest to provide a balance of the level of protection to the bees that does not compromise the taste and quality of honey produced for inter alia, human consumption. This balance does not appear to be achievable using conventional methods of controlling bee pests, such as *varroa* mite infestation, and particularly *Varroa destructor* infestation of the bees and of the hive.

It is therefore an object of the present invention to provide a more acceptable method for controlling bee pests, such as exo-parasites that infest bees like *varroa* mites and tracheal mites (e.g. *Varroa destructor* and *Acarapis woodi*), without compromising the underlying quality and overall integrity of the honey that is produced by the bees. This and other objects of the invention will become apparent from the foregoing description.

According to the present invention there is provided a method of delivering a biologically active chemical agent to an arthropod pest of a bee comprising exposing a surface of the said bee to carnauba wax particles having a volume mean diameter of at least 10 μm comprising at least one biologically active chemical agent, wherein the bee delivers the biologically active chemical agent to the arthropod pest characterized in that the carnauba wax particles consist essentially of 89.5-99.4% by weight of carnauba wax;

≤10% by weight of biologically active chemical agent; and 0.5% by weight of flow agent.

Preferably, the carnauba wax particles employed in the method of the invention consist essentially of 91.5-99.0% by weight of carnauba wax;

≤8% by weight of biologically active chemical agent; and 0.5% by weight of flow agent. Preferably still, the carnauba wax particles employed in the invention consist essentially of 93.5%-99.0% by weight of carnauba wax;

≤6% by weight of biologically active chemical agent; and 0.5% by weight of flow agent. Most preferably, the carnauba wax particles of the invention consist essentially of 93.5%-97.5% by weight of carnauba wax; 2-6% by weight of biologically active agent; and 0.5% by weight of flow agent.

Included within the term "biologically active chemical agent" are pesticides suitable for use against exoparasite species such as *varroa* mites e.g. *Varroa destructor*, and tracheal mites such as *Acarapis woodi* and the like.

By the term "pesticide" as used herein is meant any substance which can be used in the control of bee hive pests, including *varroa* mites, that are capable of infesting bees and/or bee hives, and in particular, in controlling the mite, *Varroa destructor*, that infests the species *Apis mellifera* and commercial and domestic beehives housing strains of this species. Thus, 'pesticides' include acaricides (miticides), ovicides active against mite ova, mite growth regulators, essential oils, or any combination of two or more thereof. In particular, the pesticide of use in the present invention is an essential oil that may be selected from oils such as oil of rosemary, cedarwood oil, camphor oil, camomile oil, thymol, menthol or any combination thereof. Especially preferred pesticides of use in the present invention are menthol and thymol (also referred to as 'thyme oil'), with thymol being most preferred.

The biologically active agent is selected to have a population controlling action against tracheal mites and/or *varroa* mites that affect commercial and domestic strains of *Apis mellifera* species. Preferably, the biologically active agent is selected from menthol and thymol or a combination thereof. Most preferably, the biologically active agent is thymol.

The flow agent may be any acceptable flow agent commonly employed in the art. Such flow agents may be selected from hydrophilic precipitated silicas, for example Sipernat 383 DS, Sipernat 320, EXP 4350, and Sipernat D-17 and the like.

The arthropod pest such as a mite as herein described may be exposed to the biologically active chemical agent prior to egg hatch; during egg hatch; at any stage thereafter; or a combination thereof.

In a further aspect of the invention there is provided a population of composite carnauba wax particles for use in a method according to the invention that consist essentially of:

89.5-99.4% by weight of carnauba wax;

≤10% by weight of biologically active chemical agent; and 0.5% by weight of flow agent wherein the composite particles have a VMD of at least 10 μm. Preferably, a population of composite carnauba wax particles according to the invention consists essentially of: 91.5%-99.0% by weight of carnauba wax; ≤8% by weight of biologically active chemical agent; and 0.5% by weight of flow agent. Preferably still, a population of composite carnauba wax particles according to the invention consist essentially of: 93.5%-99.0% by weight of carnauba wax; ≤6% by weight of biologically active chemical agent; and 0.5% by weight of flow agent. Most preferably a population of composite carnauba wax particles according to the invention consists essentially of: 93.5% -97.5% by weight of carnauba wax; 2-6% by weight of biologically active agent; and 0.5% by weight of flow agent. Preferably, the populations of carnauba wax particles as discussed above have a volume mean diameter (VMD) in the range of 10 μm to 100 μm. Preferably the VMD of the particle lies within the range of 10 μm to 15 μm.

The population of composite carnauba wax particles of the invention include at least one biologically active chemical agent selected from acaricides (miticides), ovicides active against mite ova, mite growth regulators, essential oils, or any combination of two or more thereof. Preferably, the population of composite carnauba wax particles according to the invention has as a chemical agent one that is selected from the group of essential oils: oil of rosemary, cedarwood oil, camphor oil, camomile oil, menthol or thymol or a combination of thymol and at least one other oil thereof. Preferably, the biologically active chemical agent of use in the invention is the essential oil thymol.

In a further aspect of the invention there is provided a method of substantially maintaining honey flow in a hive by controlling the population of arthropod pests therein by exposing the said pests to composite particles of the invention as herein described.

"Controlling the population of arthropod pests" means that the arthropod pest population is reduced in size by the pests coming into contact with the biologically active chemical agent that is comprised on the composite particles.

"Substantially maintaining honey flow" means that the operation of the hive continues without deleterious effect to the working ability of bees (and thus the hive) to collect nectar and pollen, and inter alia to make honey.

In a further aspect of the invention there is provided use of composite particles of the invention in maintaining honey flow in a hive that is infested with arthropods. Typically, the arthropods are mite species selected from *Varroa destructor* and *Acarapis woodi.*

The target site or the present invention may be a target organism, for example, a *varroa* mite, such as *Varroa destructor*, or it may be a discrete location, such as a plant or a honeycomb on which the organism is found. Typically, the target organism is a parasite of the species *Apis mellifera*, such as *Varroa destructor* or *Acarapis wood.*

The bees of use in the invention are typically physiologically sterile. The worker bees alone may be selected for use in the invention, since they are physiologically sterile. However, drone bees may also be selected for use in the invention even though such bees are not physiologically sterile.

It will be apparent to the person skilled in the art that since the bee is the carrier of the biologically active chemical, the method of the present invention may be advantageous over prior art methods because the behaviour of the bee can be utilized to deliver the biologically active agent(s) to the target organism or environs thereof. For example, where the behaviour of the bee can be utilized to deliver the biologically active agent(s) to the target organism one may use lower doses of the biologically active chemical with concomitant minimal disruption to honey flow. Furthermore, the natural grooming action of bees will also tend to help with the dispersal of particles of the invention in the hive and with the removal of mites from the bee. Thus, by using carnauba wax particles, the biologically active chemical is brought directly to the sites where the arthropod is attacking the bees and by using a powder formulation of the invention, it has been shown that the powder has the physical effect of reducing the ability of the mite to grip onto the bee cuticle. Thus, the use of a powder formulation of the invention has a physical effect on the ability of the mites to infest the bee that acts in conjunction with the miticidal action of the biologically active chemical to provide an efficient pesticide against mites that infest bees.

By the term "discrete location" as used herein is meant a location wherein the target organism lives, feeds, inhabits, or wherein it can be found. This may include for example, a field, a crop, a honeycomb, a nest, a plant, a hive, structural timbers, or a mound.

The carnauba wax particles may be capable of releasably adhering to the bee such that the carnauba wax particles comprising the biologically active agent may be delivered to the target site, i.e. to the *varroa* mite and/or its environs, such as the combs within the hive. Alternatively the carnauba wax particles may be retained on the bee and the biologically active agent may be released from the said particles.

By the term "releasably adheres" as used herein is meant any form of temporary attachment to the bee, for example, the attractive force may be electrostatic, hydrophobic, hydrophilic, chemical or physical.

The particles of the present invention as alluded to hereinabove consist essentially of carnauba wax particles and biologically active chemical agents that may be incorporated in the particle by methods including the use of solvents.

Alternatively, the particle may be a composite particle comprising a core of carnauba wax. The carnauba wax may have the biologically active agent associated with it by way of mixing, or the biologically active agent may be, for example, adsorbed thereon or absorbed therein; and/or it may be coated with the biologically active agent. The term "coated" as used herein includes a partial coating of the particle.

It will be understood that the particles may be micronised down to a preferred size, range, weight or shape, such that they may detach more easily from the surface of the bee on contact. If the particles are too small then they may become hazardous to bee health as well as human health, whilst too large they will tend to fall off the bee before the bee reaches the target site or not attach at all.

Preferably, the particles have a VMD in the range of from 10 to 100 μm. More preferably, the particles have a VMD in the range of 10 to 15 μm and any value in between, such as 10, 11, 12, 13, 14 or 15 μm and the like.

Where a chemical or naturally occurring acaricide is used, the amount of biologically active agent associated with the particles will range from 0.1 to 10% by weight as alluded to hereinbefore. Where an essential oil is used, in order to ensure efficacy, the quantity will preferably be ≤10% by weight. Where the essential oil is thymol, thymol will be present in ≤10% by weight, preferably in ≤8% by weight, and most preferably from 2-6% by weight.

In the method of the present invention the carnauba wax particles may be transferred from the bee to the target organism or to a site within the hive.

There now follow examples and figures illustrating the invention. It is to be understood that the teaching of the examples and figures is not to be construed as limiting the invention in any way.

FIG. 1: Mean percent reduction in mite populations within beehives following *varroa* mite treatments.

Figure 2:
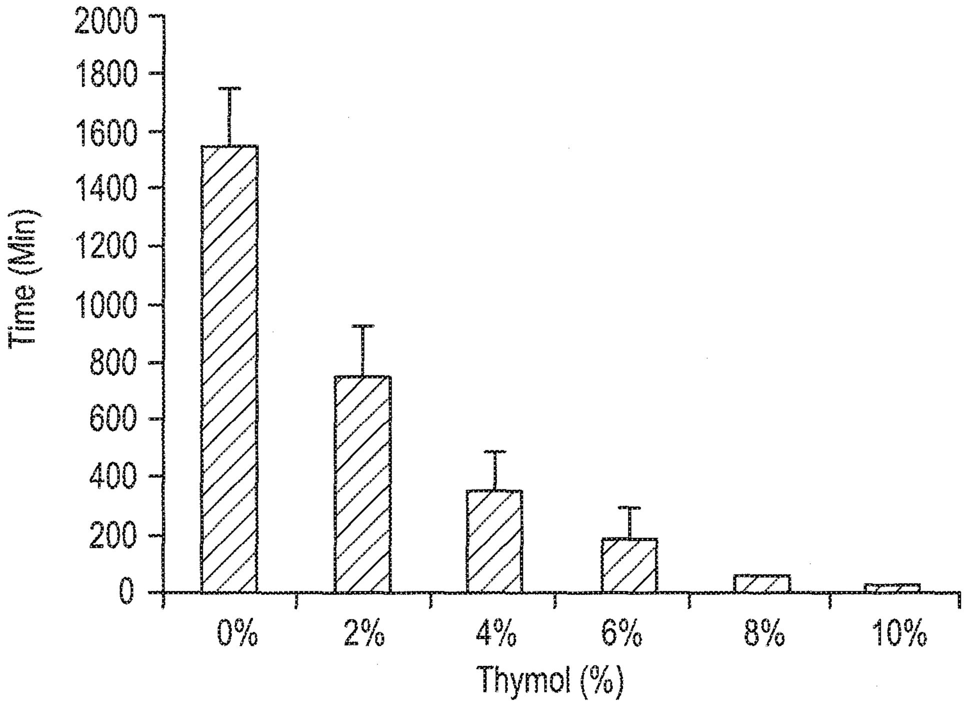

FIG. 2: Time taken for *varroa* mites to die following treatment with 0, 2, 4, 6, 8 and 10% thymol by weight in carnauba wax powder.

EXAMPLES

Evaluation of the Impact of Carnauba Wax Loaded with Thymol (6% by Weight) on Varroa Mite (*Varroa destructor*) Populations and Honeybee (*Apis mellifera*) Colonies in Beehives Trial Summary The objective of this study was to evaluate the efficacy of carnauba wax loaded with thymol (6% by weight) for the control of *Varroa destructor*, a parasite of *Apis mellifera* L. This field test was designed to give a relative indication of the ability of the test product to reduce infestation levels of this pest under field conditions, and to monitor side effects of the treatment on the bee colony.

Thirty, pre-measured foil packets containing carnauba wax loaded with thymol (6% by weight) were used for the study. Each packet was designed for one application to an individual hive, and consisted of a pre-measured dosage of 20 g of carnauba wax powder per packet containing Thymol at 6% by weight active ingredient. The wax formulation was micronised on the toll formulation mills built by Hosokawa Micron Limited, Runcorn, UK at Hosokawa Micron Limited; producing a particle size volume mean diameter >10 microns.

The study was conducted in one apiary. The location contained a treated group, a reference (positive) control group, and an un-treated control group, each containing 15 hives. Two applications each of carnauba wax containing Thymol at 6% by weight ("carnauba wax/thymol") at 20 g per 10 frame hive and Apiguard® (positive control) at 50 g per hive were made.

The carnauba wax/thymol test substance, in electrostatic powder form, was sprinkled directly over the top of the brood frames. The electrostatic powder acted as a carrier for the active ingredient Thymol at 6%. The Apiguard® was placed on top of the brood frames.

Prior to application of treatment, 300 bees from 3 different combs within each colony were collected to estimate percentage infestation by *varroa* mite of experimental colonies. If brood was present, 3 samples of 200 capped worker cells from 3 different combs were opened to find brood infestation. Based on the results, the colonies were divided into 3 groups, with each group containing similar variability in *varroa* infestation, ranging from low to high infestation. Evaluations of *varroa* mite infestation were conducted using white boards placed under each selected hive to record natural mite fall and mite mortality. Natural bee mortality was established by counting the number of bees removed by the population via the front of the hive and dropped into a wooden box at the entrance to the hive. After the first treatment application, all hives were monitored for 13 days for *varroa* mite infestation using the white board method to collect dead mites; Dead bees were collected using an empty hive super at the entrance to the hive. The colonies were then treated again and all hives were monitored for a further 13 days for *varroa* mite infestation and dead bee levels. Thirteen days following the second treatment, natural mite fall was monitored in all hives using white boards, and dead bees were monitored using empty supers for a further 2 days. On day 28, all hives were destroyed using sulphur burned within each hive over night. The number of mites remaining on the bees and brood in each hive was counted, giving a final mite population within the colonies.

Statistical analysis revealed that carnauba wax/thymol was comparable with the Apiguard treatment both statistically and numerically at the conclusion of the trial with regards to reduction in mean mite levels (P=0.972) (FIG. 1).

Treatment with carnauba/thymol resulted in significantly greater mite drop 24 h following the first and second treatment applications compared to Apiguard and the control group, (P<0.0001). There was no significant difference between all treatment groups in mean bee population reduction (P=0.216). The carnauba/thymol treatment resulted in significantly greater mean *varroa* mite drop after 24 h compared to the Apiguard and the control treatments, showing the product can be used as an immediate emergency treatment.

The overall mean temperature during the period of treatment was 16.9° C. close to 15° C.; the minimum temperature recommended for use with Apiguard.

Conclusion

Based on the parameters of this study it can be concluded that carnauba/thymol is as effective as Apiguard after two treatment applications through a 28 day period to significantly reduce *varroa* mites populations, with a reduction in mite population of 61% and 60% in the carnauba/thymol and Apiguard treatments respectively, compared to a natural decline of 35% in the control group. Within 24 h post application of the first and second treatments, the carnauba/thymol treatment significantly increased *varroa* mite drop compared to both the Apiguard and control groups.

The mite fall seen after 24 h of treatment shows that the product can be used as an instant treatment to control *varroa* mites if such a treatment is required. The product could be used before a colony is moved for pollination purposes.

2. Thymol Residues after Carnauba Wax/Thymol and Apiguard Treatment

Experiment

The objective of the study was to compare the levels of thymol residue in honey during and after treatment with the carnauba/thymol formulation and a conventional thymol based product Apiguard.

Reagents

All the reagents used for the assay were of analytical-reagent grade (>99%). Thymol was purchased from Fluka (Germany) and the stock solutions of these compounds were prepared in GC-grade acetone, obtained from Merck (Germany), Styrene from Aldrich (Germany) was used as the internal standard and its stock solution was prepared in acetone at a concentration of 50 $\mu g\ l^{-1}$. The purified water that was used in all experiments was produced by a Millipore Simplicity 185 system.

Apparatus

A Purge & Trap system (O.I Analytical, 4500) connected with an autosampler (O.I 4552) was used for the isolation of the volatile compounds. The isolated analytes collected on a trap (Tenax TA, 100 mg) and the extracted compounds were separated on a fused silica capillary column HP-5MS (30 m×0.25 mm, df=0.25 mm), using the Agilent model 6890 gas chromatograph. The detection was carried out using the Agilent model 5973 mass spectrometer and the data were acquired and processed with ChemStation program.

Determination of Thymol 10 g of each sample were weighed and diluted with 7 g of water. The solutions were transferred to the 25 ml glass tube, where a 25 μl volume of the internal standard solution was added and the mixtures were homogenized by vortex mixing. Then the solutions were transferred to the Autosampler—Purge & Trap system for the extraction of thymol. The isolation was achieved under the following conditions: purge flow (He): 30 ml/min, purge time: 40 min, purge time: 40 min, desorption temperature: 180° C. desorption time 7 min. The separation was performed with the following temperature program: initial temperature 40° C. (5 min), then rose to 120° C. at 8° C. $min^{-1}$, to 280° C. at 15° C. $min^{-1}$ (5 min). Helium was used as a carrier gas at a flow of 1 ml $min^{-1}$ and the injector temperature was 220° C. The separated compounds detected by the mass spectrometer. The temperatures in the source and quadropole were 150° C. and 230° C. respectively. Electron impact mass spectra were recorded at 70 eV.

For the quantitative analysis a 6-level calibration curve was carried out by spiking aliquots of isoglycose with known concentrations of the analytes. Spiked working standard solutions used for calibration were prepared as follows: Aliquots of 10 g of isoglocose were diluted with 7 g of water then the solutions spiked with a standard solution of thymol, in acetone, at final concentrations of 0.001, 0.2, 0.7, 1.5, 2.3, and 3 mg $g^{-1}$. These solutions were analysed using the above conditions for the extraction and chromatographic determination. Linearity was held between 0.001 and 3.0 mg $kg^{-1}$ honey and the 6-level calibration curve was y=0.239337x−0.019906, with satisfactory value for the $R^2$ (0.9925). The limit of quantitation (LOQ) was 0.001 mg $kg^{-1}$.

Trial Procedure

The study was conducted in one apiary, located at the Aristotle University Beekeeping Laboratory. The location contained a treated group, a reference (positive) control group, and an un-treated control group, each containing 15 hives. Two applications each of carnauba wax/thymol at 20 g per 10 frame hive and Apiguard® (positive control) at 50 g per hive were made 13 days apart.

The carnauba wax/thymol, in electrostatic powder form, was sprinkled directly over the top of the brood frames. The electrostatic powder acted as a carrier for the active ingredient Thymol at 6%. The Apiguard® in pre-measured tins was placed on top of the brood frames.

At the end of the trial all hives were killed to determine residual mite population.

Collection of Samples

Since residues are unevenly distributed within the combs of the hive, pool samples were collected in the following way: pieces of comb were cut with a sharp knife from all the combs with honey of the colony. Honey was obtained from these pieces of comb by dripping through a fine mesh in the laboratory.

Samples were collected on the days 0 (before first treatment), 12, 24, 36 and 48 from live colonies of each group treated as described.

Results

Results are presented in table 1. Thymol was not found in all colonies after the first treatment. Individual values for thymol residues were never over the taste threshold (2 mg $kg^{-1}$) in the carnauba wax/thymol trial, while it was higher than the threshold in one sample treated with Apiguard. The mean values after 24 days treatment were 0.3680 mg $kg^{-1}$ for carnauba wax/thymol and 1.1198 mg $kg^{-1}$ for Apiguard. After 48 days of the treatment residues fell in both trials to 0.1140 and 0.7699 mg $kg^{-1}$ respectively and only one sample from the Apiguard treated hives exceeded the Swiss tolerance value of 0.8 mg $kg^{-1}$. The considerable variation in the residue level from bee hive to bee hive might be influenced by the size of the colony and the size of brood nest. These two factors affect relative humidity, temperature and air circulation within the colony which has an effect on the evaporation of thymol.

TABLE 1

| Mean thymol residue levels in honey, mg $kg^{-1}$ | | | | | |
|---|---|---|---|---|---|
| Treatment | No. Days after first treatment applied | | | | |
| group | 0 | 12 | 24 | 36 | 48 |
| Control | 0 | 0 | 0 | 0 | 0 |
| Carnauba Wax/thymol | 0 | 0.1888 | 0.3680 | 0.2641 | 0.1140 |
| Apiguard | 0 | 0.7162 | 1.1199 | 1.0410 | 0.7699 |

As Table 1 clearly demonstrates, the technology may be useful in maintaining honey flow and keeping the level of thymol significantly below the Swiss tolerance value 2 Efficacy of 2-10% Thymol in Carnauba Wax on Varroa Mite Fall from Honey Bees The objective of this experiment was to compare the efficacy of different levels of thymol in carnauba wax on *varroa* mite fall from honey bees and consequent mortality using a laboratory based bioassay. A second objective was to evaluate the impact of the thymol concentration on bee health.

Each replicate comprised eight bees and four *varroa* mites that were placed together within plastic cups. Carnauba powder containing either 0 (vehicle control), 2, 4, 6, 8 or 10% thymol and 0.5% flow agent was sprinkled over the bees. There was also an untreated control group. The resultant mite drop from the bees was recorded. Mortality of both bees and *varroa* was monitored.

Varroa mite drop was greater in thymol treated groups compared to controls. Mite fall 1 min following treatment ranged between 29.7% for the vehicle control (blank powder) to 66.7% for 10% thymol powder. Two hours following treatment mite fall reached a plateau in all thymol treated groups, ranging between 85.1 to 96.3% of the total mite fall. Varroa drop was greater in the vehicle control compared to the negative control, indicating the powder had a physical effect that increased mite fall.

Increasing thymol content decreased the time it took for the *varroa* mites to die. When 10% thymol powder was used, mite death occurred on average 22.5 min following treatment; 2% thymol resulted in an average mortality rate of 753 min, suggesting thymol had an acaricidal effect on the Varroa mites. The mites that fell in the vehicle control took on average 25.7 hours to die, suggesting that carnauba wax alone was not acaricidal (FIG. 2).

The invention claimed is:

1. A method of delivering a biologically active chemical agent to an arthropod pest of a bee, wherein the arthropod pest is located at a discrete location selected from a field, a crop, a honeycomb, a nest, a plant and a hive, comprising:

exposing a surface of the bee to carnauba wax particles in powder form having a volume mean diameter of at least 10 μm and comprising at least one biologically active chemical agent, wherein the bee delivers the biologically active chemical agent to the arthropod pest, and wherein the carnauba wax particles consist essentially of:

89.5-99.4% by weight of carnauba wax;

≤10% by weight of biologically active chemical agent; and 0.5% by weight of flow agent.

2. A method according to claim 1, wherein the carnauba wax particles consist essentially of:

91.5%-99.0% by weight of carnauba wax;

≤8% by weight of biologically active chemical agent; and 0.5% by weight of flow agent.

3. A method according to claim 2, wherein the carnauba wax particles consist essentially of:

93.5%-99.0% by weight of carnauba wax;

≤6% by weight of biologically active chemical agent; and 0.5% by weight of flow agent.

4. A method according to claim 3, wherein the carnauba wax particles consist essentially of:

93.5%-97.5% by weight of carnauba wax;

2-6% by weight of biologically active agent; and 0.5% by weight of flow agent.

5. A method according to claim 1, wherein the arthropod pest is a species of *varroa* mite or a species of tracheal mite.

6. A method according to claim 5, wherein the biologically active chemical agent is selected from pesticides for use against *varroa* mite species and *varroa* mite behaviour modifying agents, or a combination of two or more thereof.

7. A method according to claim 6, wherein the pesticide is selected from acaricides (miticides), ovicides active against mite ova, mite growth regulators, essential oils, or any combination of two or more thereof.

8. A method according to claim 7, wherein the pesticide is selected from the essential oils: oil of rosemary, cedarwood oil, camphor oil, camomile oil, menthol or thymol or a combination of thymol and at least one other oil thereof.

9. A method according to claim 1, wherein the biologically active chemical agent is thymol.

10. A method according to claim 1, wherein pest control is caused by transference of the biologically active chemical agent from the bee to the arthropod pest.

11. A method according to claim 7, wherein the mite is exposed to the biologically active agent prior to egg hatch; during egg hatch; or at any stage thereafter; or a combination thereof.

12. A method according to claim 1, wherein the carnauba wax particles have an average particle size diameter in the range of from 10 to 100 μm.

13. A method according to claim 12, wherein the carnauba wax particles have an average particle size diameter of 10 to 15 μm.

14. A method according to claim 13, wherein the carnauba wax particles have an average particle size diameter of 10 to 12 μm.

15. A method according to claim 1, wherein the carnauba particle are each composite particles and comprises a core of carnauba wax which is impregnated with and/or coated with the biologically active agent.

16. A method according to claim 1, wherein the flow agent is selected from hydrophilic precipitated silicas.

17. A method of substantially maintaining honey flow in a hive comprising:

controlling the population of arthropod pests in said hive by exposing the said pests to populations of carnauba wax particles in powder form that consist essentially of:

89.5-99.4% by weight of carnauba wax;

≤10% by weight of biologically active chemical agent; and 0.5% by weight of flow agent, wherein the carnauba wax particles have an average particle size diameter in the range of 10 to 100 μm.

18. A method according to claim 17, wherein the arthropod pests are mite species selected from *Varroa destructor* and *Acarapis woodi.*

* * * * *